United States Patent [19]  [11] 4,322,351
Miller et al.  [45] Mar. 30, 1982

[54] ANTINEOPLASTIC 4'-FORMYLAMINO AND 4'-ACETYLAMINO VLB, AND DERIVATIVES THEREOF

[75] Inventors: Jean C. Miller; Koert Gerzon, both of Indianapolis, Ind.

[73] Assignee: Eli Lilly and Company, Indianapolis, Ind.

[21] Appl. No.: 180,789

[22] Filed: Aug. 25, 1980

[51] Int. Cl.$^3$ .................. A61K 31/475; C07D 519/04
[52] U.S. Cl. .................................. 424/262; 260/244.4
[58] Field of Search ...................... 260/244.4; 424/262

[56] References Cited

U.S. PATENT DOCUMENTS 4,075,214  2/1978  Katner et al. .................... 260/244.4
4,166,810  9/1979  Cullinan et al. ................. 260/244.4
4,203,898  5/1980  Cullinan et al. ................. 260/244.4

OTHER PUBLICATIONS

Mangeney et al., J. Am. Chem. Soc., vol. 101, No. 8, pp. 2243–2245, 4/11/79.
Conrad, et al., J. Med. Chem., vol. 22, No. 4, pp. 391–400, (1979).

Primary Examiner—Donald G. Daus
Assistant Examiner—Diana G. Rivers
Attorney, Agent, or Firm—James Lincoln Rowe; Arthur R. Whale

[57] ABSTRACT

4'-Substituted VLB and vincristine, 4-desacetyl VLB, 4-desacetylvincristine and amides and hydrazides thereof, prepared by action of HCN or acetonitrile under strongly acidic conditions.

7 Claims, No Drawings

ANTINEOPLASTIC 4'-FORMYLAMINO AND 4'-ACETYLAMINO VLB, AND DERIVATIVES THEREOF

BACKGROUND OF THE INVENTION

The alkaloids obtainable from *Vinca rosea* represent one of the most productive areas of chemistry for drugs which adversely affect the growth of experimental malignancies in mammals. Initially, only some of the alkaloids obtainable from the leaves of the plant by extraction and purifiable by chromatography were found to be active. These active anti-neoplastic vinca alkaloids obtained directly from the plant have been found to be dimeric indole-dihydroindole alkaloids representable by the formula:

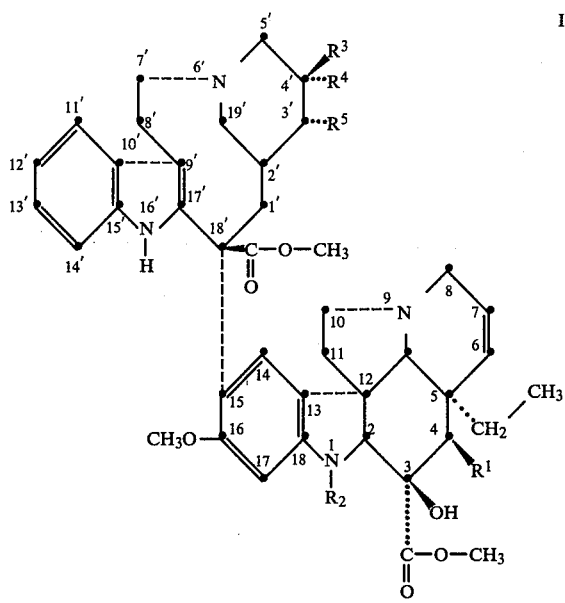

In the above formula where $R^1$ is acetoxy, $R^2$ is methyl, $R^3$ is hydroxyl, $R^4$ is ethyl and $R^5$ is H, vinblastine (vincaleucoblastine, VLB) is represented; where $R^1$ is acetoxy, $R^2$ is formyl, $R^3$ is hydroxyl, $R^4$ is ethyl and $R^5$ is H, vincristine is represented; where $R^1$ is acetoxy, $R^2$ is methyl, $R^3$ is ethyl, $R^4$ is hydroxyl, and $R^5$ is H, leurosidine is represented; where $R^1$ is acetoxy, $R^2$ is methyl or formyl, $R^3$ is ethyl and $R^4$ and $R^5$ taken together form an α-epoxide ring, leurosine and leuroformine, respectively are represented. Literature references to the above alkaloids are as follows: leurosine (U.S. Pat. No. 3,370,057), VLB (U.S. Pat. No. 3,097,137), leuroformine (Belgian Pat. No. 811,110); leurosidine (vinrosidine) and leurocristine (to be referred to hereafter as vincristine) (both in U.S. Pat. No. 3,205,220).

Two of the above alkaloids, vinblastine and vincristine, are now marketed for the treatment of malignancies, particularly the leukemias and related diseases, in humans. The two marketed alkaloids are customarily administered by the iv route. Two others, leurosidine and leuroformine, have been on clinical trial in the U.S. or in Europe.

Chemical modification of the Vinca alkaloids started slowly for several reasons. In the first place, the molecular structures involved are extremely complex, and chemical reactions which modify one specific functional group of the molecule without affecting other groups have been difficult to develop. Secondly, dimeric alkaloids lacking desirable chemotherapeutic properties have been recovered or produced from *Vinca rosea* extracts, and a determination of their structures has led to the conclusion that these inactive compounds are closely related structurally to, or even isomeric with, the active alkaloids.

One of the more recent, and more successful, modifications of the basic indole-dihydroindole structure has been the preparation of C-3 carboxamide and carboxhydrazide derivatives. Many of these carboxamides are active anti-tumor agents (see U.S. Pat. No. 4,166,810, and Conrad et al., *J. Med. Chem.*, 22, 391 (1979). In particular, 4-desacetyl VLB C-3 carboxamide (vindesine) is very active and is currently on clinical trial in humans.

U.S. Pat. No. 4,029,663 discloses three anhydro derivatives each of 4-desacetylvinblastine, 4-desacetylvincristine and 4-desacetylleurosidine. These derivatives were prepared by the action of cold concentrated sulfuric acid on vinblastine, vincristine or leurosidine. Three different double bond isomers were formed and were designated as, in the case of VLB, 3',4'-anhydro 4-desacetyl VLB; 4',20'-anhydro 4-desacetyl VLB (isomer 2); and 4',20'-anhydro 4-desacetyl VLB (isomer 1). The 4',20' isomers are double bond isomers in which the 21'-methyl is either cis or trans (above or below the plane of the vinblastine molecule).

Potier, and Kutney and research groups associated with these two men have prepared a 3',4'-anhydrovinblastine by the use of a Polonovski fragmentation reaction involving reaction of an $N_b$-oxide of catharanthine and vindoline in the presence of trifluoroacetic acid—see, for example, *J.C.S. Chem. Comm.* 670 (1975); British patent specification No. 1,536,407; *Tetrahedron Letters*, 1099, 3945 (1976); U.S. Pat. No. 4,144,237; *Heterocycles*, 3, 205, 639 (1975), 6, 905 (1977).

Functionalization of the double bond in 3',4'-anhydrovinblastine has proved difficult. Recently, Potier and his research group have reported the successful conversion of this compound (called by them $\Delta^{15'(20')}$-dehydrovinblastine) to vinblastine. This work is summarized in an article appearing a *J.A.C.S.*, 101, 2243 (1979).

During the reaction of vinblastine, vincristine or leurosidine to yield the trio of double bond isomers known collectively as anhydrovinblastine, anhydrovincristine or anhydroleurosidine, a carbonium ion intermediate at C-4' is most probably formed. It is an object of this invention to utilize this transient carbonium ion in the preparation of novel 4'-derivatives of vinblastine; i.e., to contact the carbonium ion as it is formed with a specific reagent which reacts more rapidly with the carbonium ion to give new products than the alpha carbon (3' or 20') of the carbonium ion can lose a proton to yield a stable double bond. Other objects of this invention will become apparent from the following specification.

SUMMARY OF THE INVENTION

In fulfillment of the above and other objects, this invention provides compounds of the formula:

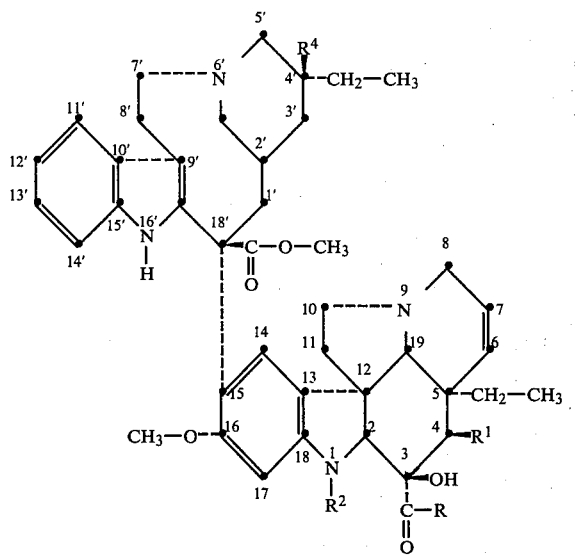

wherein
R is OCH₃, NH₂, NHCH₃, NHC₂H₅, NHC₂H₄OH or NH—NH₂,
R¹ is OH or acetoxy,
R² is CH₃ or CHO and
R⁴ is

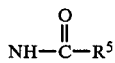

wherein R⁵ is H, methyl, NHCOO methyl or methyl-S-methyl.

Also included within the scope of this invention are the therapeutically acceptable acid addition salts of the above bases formed with non-toxic acids.

Included within the scope of this invention are the following compounds. In naming these compounds, certain shorthand notations will be used. For example, VLB containing an hydroxy at C-4 will be referred to as 4-desacetyl VLB rather than a 4-desacetoxy-4-hydroxy VLB. Similarly, an amide derivative of this invention will be referred to for example as a 4'-acetylamino VLB rather than as a 4'-deshydroxy-4'-acetylamino VLB.

4'-formylamino-4-desacetyl VLB
4'-methylthioacetylamino-4-desacetyl VLB 3-carboxamide sulfate
4'-carbomethoxyureido-4-desacetyl VLB 3-carboxhydrazide maleate
4'-carboethoxyureido vincristine
4'-methylthiomethylamino VLB succinate
4'-acetylamino-4-desacetyl VLB sulfate
4'-methylthiomethylamino-4-desacetylvincristine tartrate
4'-formylamino-4-desacetylvincristine hydrobromide
4'-acetylamino-4-desacetyl VLB 3-N-(2-hydroxyethyl)-carboxamide sulfate
4'-formylamino VLB 3-N-methyl carboxamide maleate
and the like.

Useful non-toxic acids for forming acid addition salts with the bases of this invention include inorganic acids such as: hydrochloric acid, nitric acid, phosphoric acid, sulfuric acid, hydrobromic acid, hydriodic acid, phosphorous acid and the like, as well as salts of non-toxic organic acids including aliphatic mono and dicarboxylates, phenyl-substituted alkanoates, hydroxy alkanoates and alkandioates, aromatic acids, aliphatic and aromatic sulfonic acids, etc. Such pharmaceutically-acceptable salts thus include the sulfate, pyrosulfate, bisulfate, sulfite, bisulfite, nitrate, phosphate, monohydrogenphosphate, dihydrogen-phosphate, metaphosphate, phosphite, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzene-sulfonate, toluenesulfonate, chlorobenzenesulfonate, xylenesulfonate, phenylacetate, phenylpropionate, phenylbutyrate, citrate, lactate, 2-hydroxybutyrate, glycollate, malate, tartrate, methanesulfonate, propane-sulfonate, naphthalene-1-sulfonate, naphthalene-2-sulfonate and the like salts.

Compounds according to the above structural formula in which R⁵ is methyl or methyl-S-methyl are prepared by subjecting VLB, leurosidine, vincristine or a C-3 amide or hydrazide thereof to the action of a acetonitrile or a methylthio-acetonitrile under strongly acidic conditions. These acidic reaction conditions are the same as those generally employed in carrying out a Ritter reaction. The initial reaction product is a carbonium ion at C-4'. This carbonium ion assumes the most thermodynamically stable configuration; i.e., a configuration in which the 4'-ethyl group is beta. Thus, the same carbonium ion is produced by reaction of either VLB or leurosidine since these two compounds differ only as to the configuration of the C-4'-hydroxyl and C-4'-ethyl. The same considerations hold true for each VLB amide or hydrazide and the corresponding leurosidine amide or hydrazide; regardless of which compound of a diastereomeric pair at C-4' is utilized as a starting material, only one carbonium ion is produced and only one 4'-acylamino etc. derivative prepared therefrom.

The carbonium ion produced by the action of a strong acid such as sulfuric acid upon the 4'-hydroxy group of VLB, leurosidine, vincristine or their amide derivatives, reacts rapidly with acetonitrile or a methylthioacetonitrile to yield, after workup, a 4'-methylcarbonylamino or 4'-methylthiomethylcarbonylamino derivative.

Compounds according to the above formula in which R⁵ is hydrogen cannot be prepared by the substitution of HCN for acetonitrile in the above Ritter-type reaction. Use of HCN directly under Ritter conditions yields a 4'-carbomethoxyureido derivative (R⁵ in formula I is NHCOOCH₃).

Those compounds of this invention in which R⁵ is hydrogen are prepared by somewhat different procedure wherein a sulfate salt of VLB, leurosidine, vincristine or an amide or hydrazide derivative thereof is added to liquid hydrogen cyanide to which is also added a quantity of borontrifluoride etherate. The borontrifluoride etherate acts as a Lewis acid to produce the desired C-4' carbonium ion. Under these anhydrous conditions, the carbonium ion thus formed reacts with the HCN to yield the 4'-formylamino derivative after workup.

The starting materials for preparing the compounds of this invention are readily available. VLB and leurosidine and vincristine are obtained according to the procedures of U.S. Pat. No. 3,097,137 and U.S. Pat. No. 3,205,220 respectively. The amide derivatives of VLB, leurosidine and vincristine are prepared according to the procedures as set forth in U.S. Pat. No. 4,203,898, The preferred method of preparing C-3 carboxamides of vinca alkaloids such as VLB, leurosidine and vincristine is as follows:

A C-3 carboxhydrazide is first prepared by the action of hydrazine hydrate and the alkaloid. During this reaction, the acetoxy group at C-4 is hydrolyzed to a hydroxy group. Such derivatives are named as 4-desacetyl derivatives. The C-3 carboxhydrazide group is then reacted with nitrite to yield a C-3 carboxazide. Reaction of the azide with ammonia, methylamine, hydroxyethylamine, etc. yields the corresponding carboxamide.

Since the above procedure for preparing C-3 carboxamides invariably leads to a 4-desacetyl derivative, an additional step must be employed to prepare the 4-acetoxy derivatives of the C-4 carboxamides of this invention (the above formula wherein R' is acetoxy). One method of preparing such C-4 acetoxy derivatives is to reactylate a 4-desacetyl amide with acetic anhydride or acetyl chloride in pyridine to yield the corresponding 4-acetoxy derivative. The preferred acetylation procedure is that described in U.S. Pat. No. 3,392,173 for VLB or vincristine in which a diacetyl derivative is the first product of the reaction, and this derivative is selectively hydrolyzed to yield the desired 4-acetoxy derivative. Other procedures involving selective acetylation or multiple acetylation followed by selective hydrolysis can be employed to prepare the 4-acetoxy derivatives of this invention.

There are, however, certain provisos which must be kept in mind when an acetylation of the 4-hydroxyl is desired and the C-3 carboxamide group contains an hydroxy group. In this instance, the C-4 acetylation procedure must be carried out prior to the azide-amine reaction which yields the ultimate C-3 carboxamide group. The preferred procedure here is to acylate a C-3 carboxhydrazide by standard procedures first protecting the hydrazide group itself, which would otherwise also be acylated. The preferred hydrazide protecting group is the isopropylidene group formed by reaction of the $NH_2$ portion of the hydrazide moiety with acetone. This group can be readily removed by treatment with acid or, preferably, the isopropylidene derivative itself can be reacted directly with nitrous acid to form an azide group (see U.S. Pat. No. 3,470,210, Example VII). In addition, the 4-acetoxy C-3-carboxazide thus prepared undergoes reaction with $NH_3$, $NH_2$—$C_2H_4OH$ and various other primary amines to yield compounds having the desired C-3 amide group.

Other procedures involving selective acetylation or multiple acetylation followed by selective hydrolysis or selective protection of an acetylatable function followed by acetylation and subsequent removal of the protecting group will be apparent to those skilled in the art.

Preparation of vincristine C-3 carboxamides involves some added considerations. Reaction of vincristine with hydrazine not only forms a 4-desacetyl-3-carboxhydrazide but may also partially hydrolyze the N-1 formyl group. The C-3 carboxamide prepared therefrom is readily reformylated to yield a 4-desacetylvincristine C-3 carboxamide or reacetylated and reformylated to yield a vincristine C-3 carboxamide.

Alternatively, the 4'-acylamino derivative of VLB can be oxidized at −60° C. in acetone-acetic acid with $CrO_3$ (Jovanovics, et al. procedure of U.S. Pat. No. 3,899,493) to yield the N-1 formyl (vincristine series) derivative directly or an N-1 desformyl compound which can in turn be reformylated. This procedure may not be suitable for amides containing oxidizable groups, although routine $CrO_3$ oxidations proceed very slowly if at all at −60° C.

This invention is further illustrated by the following specific examples.

EXAMPLE 1

Preparation of 4'-Acetylamino VLB

A solution containing 443.2 mg. of VLB sulfate in 6 ml. of anhydrous acetonitrile was prepared. Fifty drops of 18 M sulfuric acid were added. The resulting solution was stirred at ambient temperature for about seven hours and then was allowed to remain overnight at 0° C. Next, 6.4 g. of sodium carbonate and 40 ml. of anhydrous methanol were added. This mixture was stirred for about 15 minutes. Next, 80 ml. of a saturated aqueous sodium chloride solution were added. The reaction volume was increased to 160 ml. by the addition of water. This diluted mixture was also stirred for about 15 minutes, after which time it was extracted four times with an equal quantity of benzene. The benzene extracts were combined and the benzene removed by evaporation to yield a 381.8 mg. residue. TLC indicated that the reaction had not gone to completion (presence of VLB) so the above procedure was repeated. The product was isolated as before and a 303.7 mg. residue obtained. Three products were isolated by chromatography from this residue. The first was VLB (111.6 mg). The second was 4'-acetylamino VLB (30.8 mg.). The third product (36.2 mg.) was leurosidine (an unexpected inversion of configuration at C-4' from the VLB starting material caused by the presence of trace quantities of $OH^-$ present in the reaction mixture or during workup, reacting with the carbonium ion).

In a second preparation, 4'-acetylamino VLB obtained had the following physical characteristics:

Mass spectrum: m/e=863, 848, 849, 820, 806, 807, 792, 792, 777, 732, 7333, 674.

NMR ($CDCl_3$): δ1.87 (s, acetyl methyl), 2.09 (s, acetoxy), 2.74 (N-1 methyl), 3.60 (carbomethoxy), 3.78, 3.80, 5.25 (multiplet), 5.46 (singlet, 1H), 5.85 (multiplet), 6.09 (ring hydrogen), 6.40 (NH), 6.51 (ring hydrogen)

Infrared spectrum ($CHCl_3$) $\nu$=3675, 3435, 3400 (broad), 1740, 1660 (amide), 1618, 1585, 1505, 1460, 1440, 1375, 1045 $cm^{-1}$.

The above procedure was repeated except that 16.1 mg. of leurosidine were dissolved in 1 ml. of anhydrous acetonitrile to which was added 15 drops of 18 M sulfuric acid. The product was isolated and purified as above using proportionately smaller amounts of reagents to again yield 4'-acetylamino VLB.

Other substrates such as VLB 3-N-methylcarboxamide, 4-desacetylvincristine 3-carboxamide, 4-desacetylleurosidine 3-N-(2-hydroxyethyl)carboxamide and the like can be substituted for VLB or leurosidine in the above procedure. Similarly, propionitrile, butyronitrile, or isobutyronitrile can be substituted for acetonitrile in the above procedure to yield the corresponding 4'-acylamino derivative.

EXAMPLE 2

Preparation of 4'-Formylamino VLB

A solution was prepared by adding 16.7 mg. of VLB sulfate to 5 ml. of liquid HCN. 3 ml. of BF$_3$ etherate were added and the resulting clear pale yellow solution stirred at ambient temperature for about 16 hours. The reaction mixture was concentrated by evaporation of the volatile constituents in vacuo. Water was added and the resulting aqueous mixture made basic by the addition of 14 M aqueous ammonium hydroxide. The aqueous layer was extracted 4 times with equal volumes of methylenedichloride. The methylenedichloride extracts were combined and the solvent evaporated therefrom. The resulting residue was dried with a toluene azeotrope to yield 87.7 mg. of anhydrous material. Preparative thin layer chromatography using an ether-toluene-diethylamine-methanol (20:1:1:1) eluant produced four products. These were, in order of elution, VLB, 4-desacetyl VLB, 4'-formylamino VLB and 4'-formylamino-4-desacetyl VLB.

4'-Formylamino VLB had the following physical characteristics:

Mass spectrum: m/e=851 (transmethylation), 837, 806, 793, 792, 778, 733, 732, 678, 633, 575, 495, 494, 469, 381, 379, 336, 382, 180, 167, 149, 135, 111.

Infrared spectrum (chloroform): $\nu$ at 3670, 3470, 3390 (broad), 1735, 1680, 1615, 1500, 1455, 1435, 1370, 1040, cm$^{-1}$.

4'-formylamino-4-desacetyl VLB had the following physical characteristics:

Mass spectrum: m/e=809 (transmethylation), 795, 751, 750, 737, 736, 690, 688, 649, 633, 598, 553, 427, 382, 379, 366, 336, 295, 240, 188, 180, 174, 149, 135, 117.

Infrared spectrum (chloroform): $\nu$ 3670, 3550, 3470, 3390, 1735, 1680, 1615, 1500, 1460, 1435, 1370, 1100, 1040, 1010 cm$^{-1}$.

EXAMPLE 3

Preparation of 4'-methylthioacetylamino VLB

A solution was prepared containing 315.6 mg. of VLB sulfate in 4.0 ml. of methylthioacetonitrile. Fifty drops of 18 M aqueous sulfuric acid were added and the reaction stirred at room temperature for about 15 minutes. The reaction mixture was then added to 20 ml. of anhydrous methanol containing also 7 g. of solid anhydrous sodium carbonate. This mixture was stirred for about one-half hour after which time 100 ml. of saturated aqueous sodium chloride were added. This mixture was diluted with water to a volume of 200 ml. The resulting aqueous alkaline mixture was extracted four times with an equal volume of toluene. The toluene extracts were pooled and the toluene evaporated from the pooled extracts in vacuo to yield a residue weighing 176.7 mg. This residue was purified by preparative thin layer chromatography using an ethyl acetate-methanol (1:1) solvent as the eluant. Fractions shown to contain 4'-methylmercaptoacetylamino VLB were combined and the solvent evaporated in vacuo. 18.4 mg of 4'-Methylthioacetylamino VLB were obtained having the following physical characteristics.

Infrared spectrum (chloroform): $\mu$ at 3660, 3470, 3360, 1735, 1655 (amide), 1610, 1500 cm$^{-1}$.

Mass spectrum m/e at 911 (transmethylation), 895, 864, 838, 792, 751, 734, 634, 525, 469, 336, 282, 235, 149, 135.

In the above reaction, other alkylthioalkylnitriles can be used such as methylthiopropionitrile, ethylthioacetonitrile and the like to prepare the corresponding 4'-alkylthioacylamino VLB, vincristine or amides thereof.

EXAMPLE 4

Preparation of 4'-Methoxycarbonylureido VLB

A solution was prepared by dissolving 99.8 mg of VLB sulfate in 3 ml. of liquid HCN at room temperature. Twenty-five drops of 18 M aqueous sulfuric acid were added and the solution stirred at room temperature for 18 hours. Thin layer chromatography indicated that no VLB remained in the reaction mixture. 4'-Methoxycarbonylureido VLB was isolated and purified by the procedure of Example 3. 6.4 mg. of 4'-Methoxycarbonylureido VLB were obtained having the following physical characteristics:

Infrared spectrum (chloroform): $\nu$ at 3660 (broad), 3400, 1720, 1675, 1610 cm$^{-1}$.

Mass spectrum: m/e=910, 850, 835, 804, 790, 749, 732, 731, 672, 643, 632, 604, 522, 464, 379, 336, 293, 278, 193, 167, 150, 149, 136, 135.

The compounds of this invention are antimitotic compounds which adversely affects the growth of malignant cells. This activity is manifested in a standard mitotic inhibition test employing Chinese hamster ovary cells. 4'-Acetylamino VLB had a mitotic index + (15–25% inhibition) at $2.0 \times 10^{-2}$ mcg/ml. and 4'-acetylamino-4-desacetyl VLB had a mitotic index ++ (25–50% inhibition) at 2.0 mcg/ml.

The bases of this invention and their salts preparable by the processes disclosed herein are active in vivo against transplanted tumors in mice. To demonstrate such activity, a protocol was used involving the administration of each drug by the intraperitoneal route at selected dose levels against B$_{16}$ melanoma, 755 adenocarcinoma and P1534(CJ) and P388/V leukemias.

The following table—Table 1—gives the results of experiments in which mice bearing the susceptible transplanted tumor were treated with a compound of this invention. In the table, column 1 gives the name of the compound; column 2, the tumor used; column 3 the dosage; and column 4, the percent inhibition of tumor growth (I) or prolongation of life (PL). The following dosage regimens were employed: every day for 7 or 10 days after tumor inoculation; or every fourth day (three doses) starting at the third day after tumor inoculation.

TABLE I

| Name of Compound | Tumor | Dosage (mg/kg) regimen | | Percent Inhibition (I) or Prolongation (PL) |
| --- | --- | --- | --- | --- |
| 4'-acetylamino VLB sulfate | P1534(J) | every third day | 7.5 | 71(I) |
| | | every third day | 5.0 | 42(I) |
| | 755 | 11 days | 6 | Toxic |
| | | 11 days | 3 | 57(I) |
| | | 11 days | .5 | 33(I) |
| | | 10 days | 1 | 18(I) |

TABLE I-continued

| Name of Compound | Tumor | Dosage (mg/kg) regimen | | Percent Inhibition (I) or Prolongation (PL) |
|---|---|---|---|---|
| | | 10 days | .75 | 29(I) |
| | | 10 days | .5 | 30(I) |
| | B16 | 3 days | 3 | 74-201(PL)* |
| | | 3 days | 1.5 | 120(PL)* |
| | | | .75 | 119(PL)* |
| | P388/V | | | 20(PL)* |
| 4'-acetylamino-4-desacetyl VLB | P1534(J) | | 9.5-1.0 | 2-11(I) |
| | B 16 | 10 | 1.0 | 58(I) |
| | | | .75 | 44(I) |
| | | | .5 | 23(I) |

*= 1 or more indefinite survivors.

In utilizing the novel compounds of this invention as anti-tumor agents in mammals, the parenteral route is ordinarily employed. Prior to administration, the drug is customarily mixed with a pharmaceutically suitable carrier. With parenteral administration, the intravenous route is preferred although, with smaller mammals such as mice, the intraperitoneal route may be used. For intravenous administration, isotonic solutions containing 1-10 mg./ml. of a salt of an alkaloidal base of the above formula are employed. The drug is administered at a dose of from 0.01 to 10 mg./kg. and preferably from 0.05 to 1 mg./kg. of mammalian body weight once or twice a week or every two weeks depending on both the activity and the toxicity of the drug. An alternative method of arriving at a therapeutic dose is based on body surface area with a dose in the range 0.1 to 10 mg./meter squared of mammalian body surface administered thrice weekly or every 7 or 17 days.

As would be expected, the compounds of this invention differ in their anti-tumor spectrum from that of VLB, vincristine and leurosidine in the same way that the anti-tumor spectra of those compounds differ among themselves, one drug being more effective against certain tumors or classes of tumors and less effective against others. However, in utilizing a compound of this invention clinically, an oncologist would administer it initially by the same route, in the same vehicle and against the same types of tumors as employed clinically with vindesine, vincristine and VLB. Differences in dosage level would, of course, be based on relative oncolytic potency and toxicity.

Tumors against which clinical trial candidates are screened include adenocarcinoma of the breast, adenocarcinoma of the colon, bronchogenic carcinoma, adenocarcinoma of the pancreas, ovarian cancer, malignant melanoma, acute myelocytic leukemia, acute lymphocytic leukemia, lymphomatous disease and malignant glyoma. A compound of this invention would be tested clinically against one or more of these tumors as well as other tumors known to be susceptible to iv administration of vincristine, VLB or vindesine. After its potency, nature and degree of side effects etc. had been established, the drug would be tried against tumors for which there is no therapy. After preliminary tests were concluded and the results published, the drug would be used against tumors susceptible to its action at relatively non-toxic dose levels.

We claim:
1. A compound of the formula

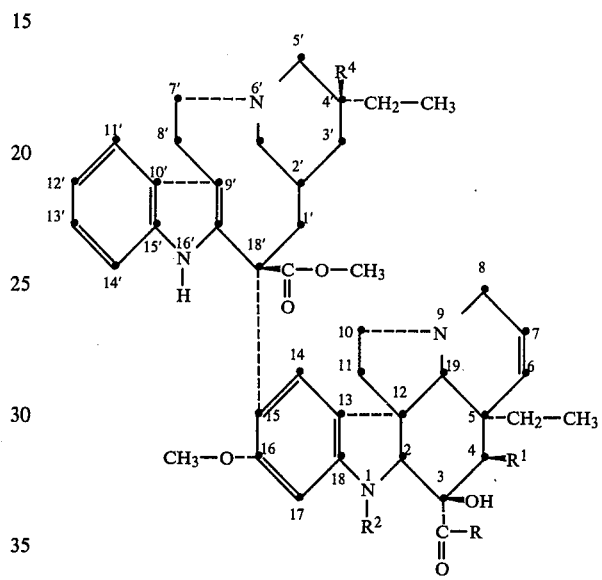

wherein
R is $OCH_3$, $NH_2$, $NHCH_3$, $NHC_2H_5$, $NHC_2H_4OH$ or $NH-NH_2$,
$R^1$ is OH or acetoxy,
$R^2$ is $CH_3$ or CHO and
$R^4$ is

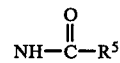

wherein $R^5$ is H, methyl, NHCOO methyl or methylthiomethyl,
and pharmaceutically acceptable acid addition salts thereof formed with non-toxic acids.

2. A compound according to claim 1, said compound being 4'-acetylamino VLB.

3. A compound according to claim 1, said compound being 4'-formylamino VLB.

4. A compound according to claim 1, said compound being 4'-methylthioacetylamino VLB.

5. A compound according to claim 1, said compound being 4'-methoxycarbonylureido VLB.

6. A pharmaceutical formulation in unit dosage form comprising per unit dose an antineoplastic amount of a compound according to claim 1 plus one or more pharmaceutical diluents.

7. A method of treating neoplasms which comprise administering to a mammal having a neoplasm susceptible to the action of a drug according to claim 1 and in need of treatment, an antineoplastically effective amount of a drug according to claim 1.

* * * * *

UNITED STATES PATENT AND TRADEMARK OFFICE
CERTIFICATE OF CORRECTION

PATENT NO. : 4,322,351

DATED : March 30, 1982

INVENTOR(S) : Jean C. Miller et al.

It is certified that error appears in the above-identified patent and that said Letters Patent are hereby corrected as shown below:

Column 6, line 45, "792, 792, 777, 732, 7333, 674" should read -- 792, 793, 777, 732, 733, 674.--

Signed and Sealed this

Twentieth Day of July 1982

[SEAL]

Attest:

GERALD J. MOSSINGHOFF

Attesting Officer

Commissioner of Patents and Trademarks